(12) United States Patent
Thramann

(10) Patent No.: US 10,470,683 B1
(45) Date of Patent: Nov. 12, 2019

(54) SYSTEMS AND METHODS TO DISASSOCIATE EVENTS AND MEMORY INDUCED REWARDS

(71) Applicant: Jeff Thramann, Longmont, CO (US)

(72) Inventor: Jeff Thramann, Longmont, CO (US)

(*) Notice: Subject to any disclaimer, the term of this patent is extended or adjusted under 35 U.S.C. 154(b) by 242 days.

(21) Appl. No.: 15/582,403

(22) Filed: Apr. 28, 2017

Related U.S. Application Data

(60) Provisional application No. 62/331,032, filed on May 3, 2016, provisional application No. 62/332,316, filed on May 5, 2016.

(51) Int. Cl.
*A61B 5/04* (2006.01)
*A61B 5/0476* (2006.01)
*A61B 5/0482* (2006.01)
*A61B 5/0484* (2006.01)
*A63F 13/28* (2014.01)

(52) U.S. Cl.
CPC ........ *A61B 5/0482* (2013.01); *A61B 5/04842* (2013.01); *A61B 5/04845* (2013.01); *A61B 5/04847* (2013.01); *A63F 13/28* (2014.09)

(58) Field of Classification Search
CPC ... A61B 5/0476; A61B 5/4836; A61B 5/0478; A61B 5/0482; A61B 5/04001; A61B 5/0006; A61B 5/486; A61N 1/36139
See application file for complete search history.

(56) References Cited

U.S. PATENT DOCUMENTS

| | | | | |
|---|---|---|---|---|
| 2002/0107454 | A1* | 8/2002 | Collura | A61B 5/0531 600/544 |
| 2009/0051544 | A1* | 2/2009 | Niknejad | G06F 3/011 340/573.1 |

OTHER PUBLICATIONS

Jeff Tyson, "How Video Game Systems Work", Oct. 16, 2000. HowStuffWorks.com. <https://electronics.howstuffworks.com/video-game.htm> Jan. 17, 2019.*
Rosen, J. "How Your Brain Might Be Secretly Thwarting Your New Year's Resolutions," John Hopkins University, downloaded from http://releases.jhu.edu/2016/02/11/how-your-brain-might-be-secretly-thwarting-your-new-years-resolutions-2/, Feb. 11, 2016, 2 pages.

* cited by examiner

*Primary Examiner* — Christine H Matthews
*Assistant Examiner* — Joshua Daryl D Lannu
(74) *Attorney, Agent, or Firm* — Perkins Coie LLP

(57) ABSTRACT

The present application is a neurological feedback system and method. The neurological feedback provides a trigger event to evoke a first neurological response from the brain of a user and a feedback event to evoke a second neurological response from the brain of a user to counter the first neurological response. As such, when the trigger event evokes a positive first neurological response, such that, for example, dopamine is released by the brain, the feedback event evokes a negative second neurological response, such that, for example, less or no dopamine is released by the brain in response the trigger event (and the converse). The neurological feedback may be useful to break additions or train a brain not to crave certain things.

19 Claims, 5 Drawing Sheets

SYSTEMS AND METHODS TO DISASSOCIATE EVENTS AND MEMORY INDUCED REWARDS

CROSS-REFERENCE TO RELATED PATENT APPLICATIONS

This application claims the benefit of U.S. Provisional Application No. 62/331,032, filed May 3, 2016, and U.S. Provisional Application filed 62/332,316, filed May 5, 2016, the disclosures of which are hereby incorporated by reference in their entirety.

BACKGROUND

Exercising the brain to prevent cognitive decline or improve focus is becoming a more common activity in today's society with applications and web pages, such as, for example, Lumosity.com. The applications are generally about stimulating the neural pathways in parts of the brain attributable to memory or focus in such a way as to strengthen and reinforce existing neural connections. The theory of brain training, in part, relies on the fact that the human brain remains plastic and creates new connections through increased stimulation of the relevant pathways.

In certain recent studies, it has been discovered that the brain tends to "think" and "pay attention" to events (actions, sounds, sensations, tastes, visuals) that produced a pleasurable or rewarding experience in the past. For simplicity, pleasurable or rewarding will be consider events (as broadly defined) that stimulate the brain to produce dopamine and other neurochemical reactions associated with pleasure or reward. In lay terms, these may be considered "feel good" activities.

Researchers at John Hopkins University conducted a study with a small sample of participants. The participants were instructed that they would be rewarded (money in this case) for certain behavior. The reward would be X for identifying "green" objects on a computer screen and 6X for identifying "red" objects on the same computer screen. The next day, the same participants were ask to find certain shapes on the screen but color was no longer relevant for the activity. The participants' brain activity was monitored using positron emission tomography ("PET"). Because of the previously associated large reward for the discovery of red objects, the research identified that the participants tended to focus on the red objects even though no reward was in fact contemplated by the on-going study. The research identified that the participants focus on red was unconscious, and the brain was stimulated by dopamine (and possibly other neuro chemical reactions associated with pleasure) when the red objects appeared.

The research further identified that the higher the dopamine or the like in the brain based on the previously rewarded behavior, the harder it was for the participant to complete the new or repurposed task. In other words, when a person sees or experiences something associated with a past reward, his/her brain flushes with dopamine unconsciously and regardless of an expectation of a reward. Because of the neurochemical reaction, the brain focuses on the event causing the reaction regardless of the conscious effort of the individual.

Such unconscious activity indicates that self-control is more difficult in activities associated with previously rewarding experiences. The research also suggests why, among other things, it may be more difficult to maintain a diet for extended periods of time or break an addiction.

The study concluded that there was an opportunity to attempt to develop a pharmaceutical to curb the neurochemical reactions associated with rewards or pleasure based on past experiences. Use of pharmaceuticals, however, may have unintended consequences including, for example, depression or the like. Thus, against this background, it would be desirous to develop systems and methods to disassociate the memory of a reward with events or objects.

SUMMARY

This Summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

In one aspect, the technology of the present application uses triggers representative of a positive event or object and incorporates a negative results into an application. In one embodiment, the positive event or object may be represented by an image. The image is incorporated into a game application with a negative implication. The game application is launched, and the trigger with the negative result is displayed in the normal course of the game. In another aspect, the trigger may be provided to the user with a corresponding negative event or object. The trigger may be an image, video, sound, smell, sensation, or the like. Similarly, the corresponding negative event or object may be an image, video, sound, smell, sensation (such as an electric shock), or the like.

These and other aspects of the present system and method will be apparent after consideration of the Detailed Description and Figures herein.

DRAWINGS

Non-limiting and non-exhaustive embodiments of the present invention, including the preferred embodiment, are described with reference to the following figures, wherein like reference numerals refer to like parts throughout the various views unless otherwise specified.

DETAILED DESCRIPTION

Figure 1:
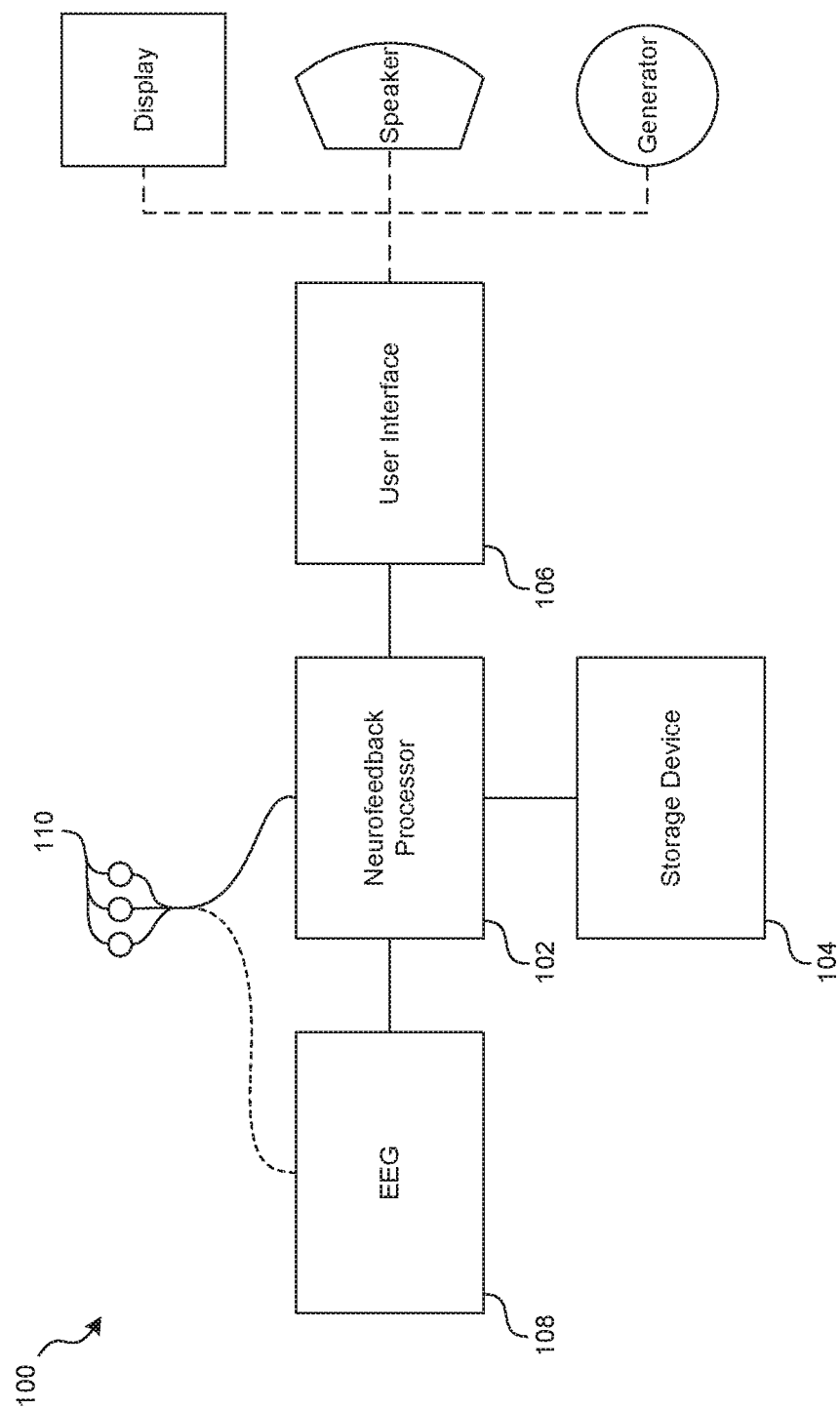
FIG. 1 is a diagram illustrating a neurofeedback system consistent with the technology of the present application.

The technology of the present application will now be described more fully below with reference to the accompanying figures, which form a part hereof and show, by way of illustration, specific exemplary embodiments. These embodiments are disclosed in sufficient detail to enable those skilled in the art to practice the technology of the present application. However, embodiments may be implemented in many different forms and should not be construed as being limited to the embodiments set forth herein. The following detailed description is, therefore, not to be taken in a limiting sense.

The technology of the present application is described with specific reference to handheld devices, such as, for example, Smartphones, handheld computers, touch devices or touch screens (such as certain smartphones, iPads, Surface, etc), and the like. However, the technology described herein may be used with other more complex devices, such as neurofeedback devices, specialty application processor, and the like. Additionally, the technology described herein is largely described with visual events, such as, for example images and video. However, the technology of the present application may be applicable to other mechanisms such as sound, smell, taste, sensations, touch, and the like. Moreover, the technology of the present application will be described with relation to exemplary embodiments. The word "exemplary" is used herein to mean "serving as an example, instance, or illustration." Any embodiment described herein as "exemplary" is not necessarily to be construed as preferred or advantageous over other embodiments. Additionally, unless specifically identified otherwise, all embodiments described herein should be considered exemplary.

In certain aspects, the technology of the present application are directed to a neurofeedback system directed by a facilitator (who may be a medical doctor or PhD) or individual to disassociate the memory of a reward with events. In one aspect, providing negative imagery when experiencing an otherwise pleasant event or a trigger for that otherwise pleasant event may facilitate disassociation of the memory of a positive experience such that the next exposure to the event will not unconsciously trigger a positive or reward based memory. In other aspects, the exposure to the event will trigger a lesser positive or reward based reaction. The disassociation of the memory and the event may further inhibit the production of dopamine and other neurochemical reactions that enhance pleasure.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated on or discussed herein. Synonyms for certain terms are provided. A recital of one or more synonyms does not exclude the use of other synonyms. The use of examples anywhere in this specification, including examples of any terms discussed herein, is illustrative only, and is not intended to further limit the scope and meaning of the disclosure or of any exemplified term. Likewise, the disclosure is not limited to various embodiments given in this specification Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

The technology of the present application disclose and describe a neurofeedback system or device that helps individuals (sometimes referred to as users, patients, clients, or the like) disassociate a memory of a reward with an event or object from the actual (or similar) event or object. For clarity, an individual may have developed a historical association between the reward of pleasure and the event of eating cake. For an individual trying to lose weight, the brain remembers the pleasant experience of eating cake and releases dopamine even though the dieter is consciously trying to avoid cake. The technology of the present application provides neurofeedback to disassociate the reward of pleasure with the event of eating cake such that the brain releases less or no dopamine, among other things when the dieter sees a cake.

In some aspects, the neurofeedback may provide imagery to cause the disassociation. For example, the imagery may first stimulate the experience using a trigger, such as an image or video of a cake (see above), and subsequently show images of cod liver oil, or other such distasteful foods, images of violence, or other images that the individual finds distasteful rather than cake, chocolate or other pleasurable foods. The distasteful imagery over time should train the brain such that the reward is disassociated, resulting in less or no dopamine being released to the brain. In other aspects, the neurofeedback may provide unpleasant feelings, such as defeat in a video game, a negative consequence in a game or application (reduction in skill, experience, gold, etc.), unpleasant sounds, such as a high pitched noise, unpleasant smells, such as a skunk odor, unpleasant sensations, such as electric shock, unpleasant touch, such as needles, or the like for the distasteful feedback. The feedback mechanism may, in certain aspects, be adjustable between different types of feedback, such as from visual to audio, or scale, such as from mildly distasteful imagery to very distasteful imagery.

FIG. 1 is a block diagram illustrating an exemplary neurofeedback system 100 for disassociating a memory (or specifically the reward based memory) of an event or object from the event or object. The system 100 comprises a neurofeedback processor 102, which may be incorporated into a smartphone, touch screen computer, laptop computer, handheld computer, or other central processing units, chip sets, or firmware. The neurofeedback processor 102 controls the major functions of the neurofeedback system 100 including the functional operations associated with the neurofeedback (or stimulus) described herein. The neurofeedback processor 102 has access to a storage device 104. Storage device 104 may be many conventional volatile or non-volatile memory systems. While dictated by context, memory as used herein may refer to either a user's memory or a processor's memory. The storage device 104 is interconnected with the neurofeedback processor 102. The storage device 104 may be integrated, remotely located, or co-located with the neurofeedback processor 102. The storage device 104 may store data necessary or convenient for operation of the neurofeedback system 100 as will be explained herein. The exemplary neurofeedback system 100 further includes a user interface 106. The user interface depends in part on how the neurofeedback system 100 is configured to trigger the memory and provide the neurofeedback. For example, if imagery is used to trigger the memory and provide the neurofeedback, the user interface 106 may be a display screen (which may be a conventional monitor or a touch screen). If audio is used to trigger the memory, the user interface 106 may be a speaker. If electrical shock is used to provide the neurofeedback, the user interface may be an electrical generator. The user interface 106 may be any combination of triggering and neurofeedback mechanisms.

Neurofeedback processor 102 also may include brain activity mapping technology, such as the aforementioned PET technology. In other aspects, neurofeedback system 100 may include electroencephalography (EEG) processor 108. The neurofeedback processor 102 and the EEG processor 108 may be integrated into a single processor or multiple processors (or servers). The EEG module 108 receives electrical signals from electrodes 110 placed strategically to monitor the user's brain electrical activity. The signals from the electrodes 110 are processed by the EEG module 108 and displayed on the user interface 106, which would include a monitor in this instance. Using the PET or EEG, the user may establish a base line brain activity related to the memory of the event that caused the release of dopamine or the like. Subsequent to the neurofeedback algorithm, an example of which is described below, the changes in the brain activity from the base line may be monitored to determine the effectiveness of the algorithm.

Figure 2:
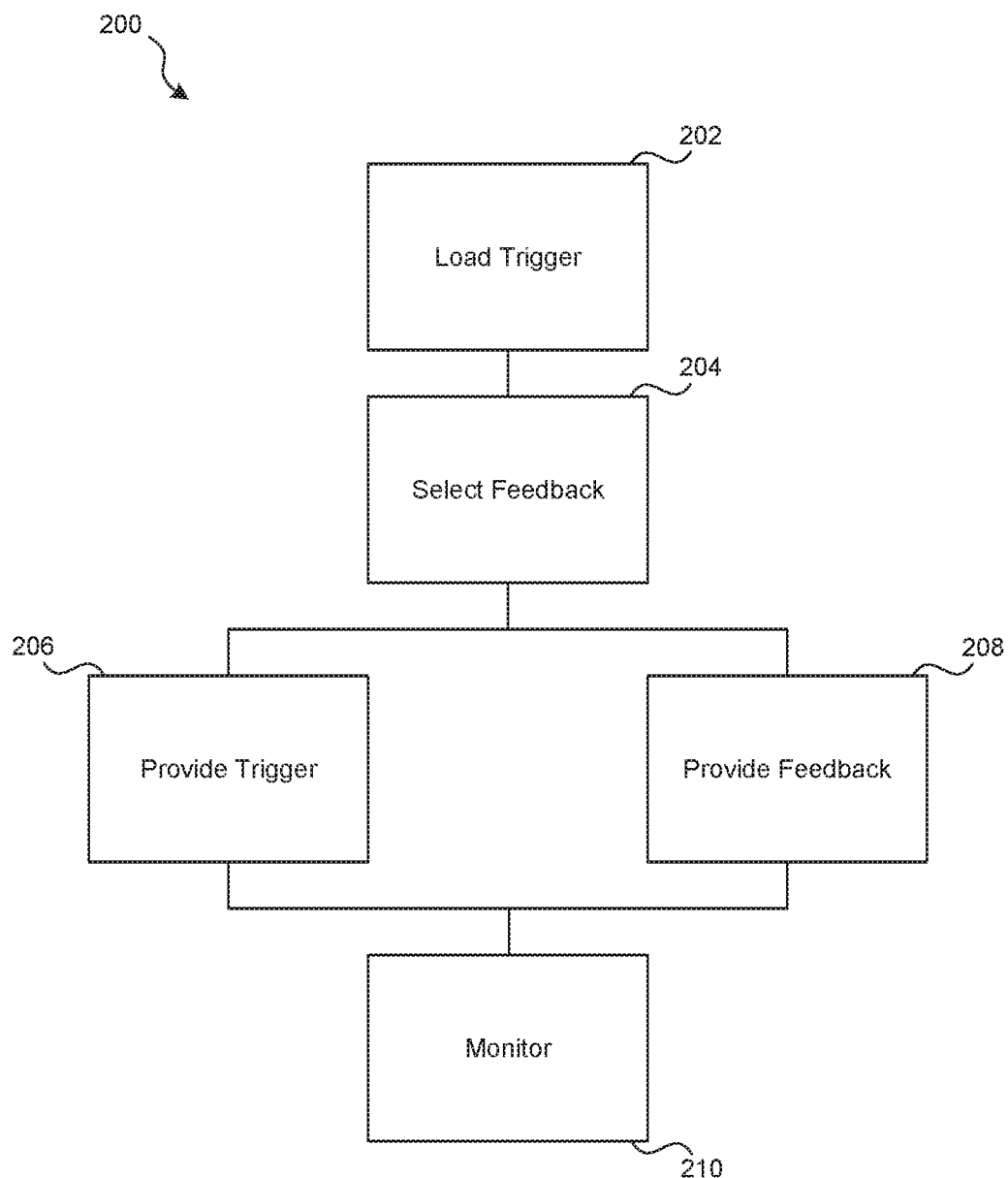
FIG. 2 is a diagram illustrating a method of using the neurofeedback system of FIG. 1.

With reference now to FIG. 2, an exemplary methodology 200 of the algorithm to disassociate a memory from a reward is now explained. First, at step 202, the neurofeedback processor 102 and memory 106 are loaded with a trigger that stimulates the memory of the event that produced a reward or otherwise pleasant experience. Alternatively, if the triggers are already loaded, the trigger is identified. In the exemplary embodiment, the trigger is deemed to be an image or video of an event, such as the cake mentioned earlier or the image incorporated in a video game such as the cake as an object in a video game, but could be, for example, scenery, buildings, clipart, drawings. In other aspects, the trigger may be a sound, such as a wedding march or a graduation procession. In still other aspects, the trigger may be a scent, such as a perfume or a home cooked meal. In yet other aspects, the trigger may be a taste or a sensation. These are only examples of possible triggers and other may exist. Next, at step 204, negative or unpleasant feedback is selected. The negative or unpleasant feedback may be as described above. One or both of the identification of the trigger and the selection of the negative or unpleasant feedback (steps 202 and 204) may be optional in applications were the neurofeedback system 100 is provided with present information.

Next, at step 206, the trigger is provided to the user. In one exemplary embodiment, the neurofeedback processor 102 would fetch from storage device 104 an image of an event, such as, for example, a sunny beach. The fetched image would be displayed on the user interface 106 for a sufficient amount of time for the user to recognize the image. At step 208, which occurs at substantially the same time (or shortly thereafter as determined by therapeutic testing), the neurofeedback processor 102 would provide the negative stimulation to the user. In one exemplary embodiment, the neurofeedback processor 102 would fetch the negative stimulation from the storage device 104, such as a dark and stormy night. The fetched negative stimulation would be displayed on the user interface 106 for a sufficient amount of time for the user to recognize the image. In one aspect, the negative imagery would disassociate the pleasurable memory of the sunny beach and replace it with the negative memory of a dark and stormy night. In other embodiments, both images would be displayed. In yet other embodiments, the images would alternate. This, it is believed, will lead to the brain producing less dopamine and other neurochemicals associated with "feeling good" because of the triggering event, which is a beach in this example. In other embodiments, the imagery would be the trigger, but the negative stimulation may be an annoying sound from a speaker user interface 106, such as fingernails on a blackboard. Finally, and optionally, the brain response may be monitored using the PET or EEG as discussed above, step 210.

Figure 2A:
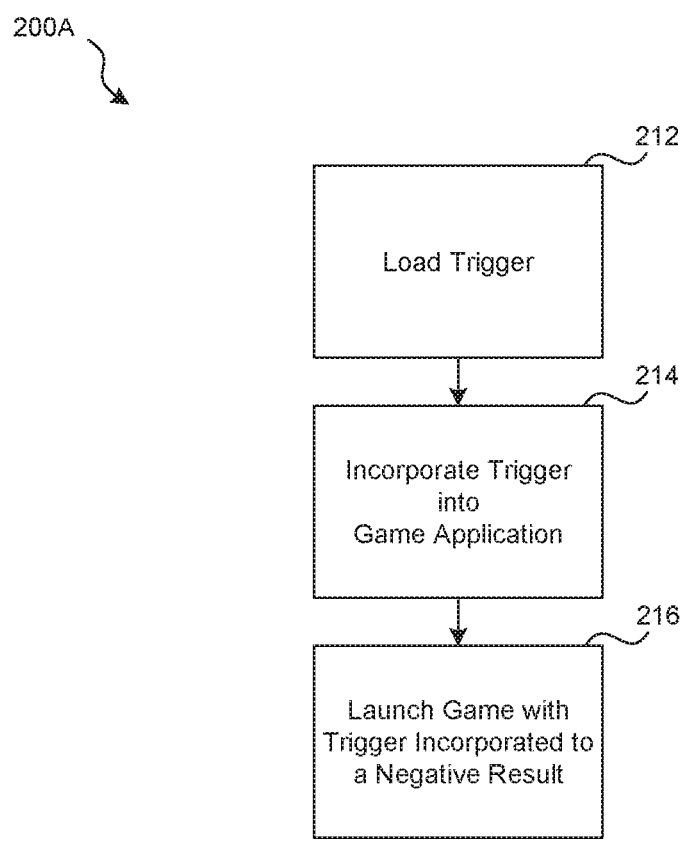
FIG. 2A is a diagram illustrating a method of using the neurofeedback system of FIG. 1.

Alternatively in FIG. 2A, another methodology 200A of the algorithm to disassociate a memory from a reward is now explained. Similar to the above, at step 212, the neurofeedback processor 102 and memory 106 are loaded with one or more triggers that stimulate the memory of the event that produced a reward or otherwise pleasant experience. Alternatively, if the triggers are already loaded, the trigger is identified. Next, the neurofeedback processor incorporates the trigger into a game application, step 214. Importantly, the trigger is NOT incorporate to provide an award, such as an increase in character experience, an increase in gold (or other monetary award), lives, or the like. Rather, the trigger is incorporated into the game application as a negative result. The neurofeedback processor next, at step 216, launches the game application with the trigger incorporated. For example, with reference back to the cake example, the image of a cake could pop up every time the user loses in a video game (losing should be defined broadly to include reductions in "heart", reductions in "hit points", reductions in money, or the like. Alternatively, the image of a cake could be something that has to be avoided or the user dies in the game. For example, the goblins in a hack n' slash game could be images of cake, or the bullets being fired at the user in a first person shooter could be images of cake, etc. In other words, the game application, whatever the situational effect, uses the trigger to create a negative association to disassociate pleasure with certain events or objects.

The technology described above generally relates to disassociation of a memory of a rewarding experience associated with an event or an object. It is believed this disassociation will lessen the likelihood that someone will continue the previously rewarding experience simply because the brain is drawn to the event or object. Similar techniques may be used to associate a memory of an event or an object with a positive or rewarding memory even when the event or the object is generally perceived to have a negative or less than pleasant experience/memory. In other words, the converse also would be able to associate negative experiences with positive memory rewards to reinforce behavior. With reference to the above figures, for example, the trigger would be replaced with an image that stimulates a negative memory and the feedback would provide a positive experience. Reversing the above, for example, the triggering image in FIG. 2 may be a foul weather night scene. The positive feedback (rather than negative in this instance) may be a sunny beach. In other aspects, the trigger and feedback may be images, audio, scent, sensations, or the like. With reference to FIG. 2A, the negative trigger would be incorporated into a game application associate with a reward, such as, for example, increased experience for the player, increased monetary awards, increase time of play, increased hit points, or the like depending on the game application. For example, hitting the broccoli in the game may cause a 5× bonus or the like. In certain aspects, for example, the feedback may be a combination of disassociation of the reward for behavior and a reward for desired behavior. For example, grabbing the icon of the cheesecake may cause a player to take damage whereas grabbing the broccoli icon may cause an increase in experience level.

In certain embodiments, wearables and sensors may contribute the feedback (positive or negative). For example, the wearable may identify a lack of movement of the individual, such as by a GPS monitor, a heart rate monitor, a breath rate monitor, or the like. The lack of movement may result in the wearable generating an unpleasant vibration that persists until such a time until the person moves. Once the person moves, the unpleasant sensation not only ceases, but positive feedback is provided, such as pleasant music or the like. Other sensors may be used to identify negative events or objects, such sensor may include pulse oxygen levels, blood glucose levels, skin resistance, heart rate or variable heart rate, or the like.

Ideally, the associations decrease behaviors that individuals desire to avoid and increases behaviors that individuals desire to encourage. As mentioned above, a single application may incorporate both features, promote disassociation only, or promote association only.

Figure 3:
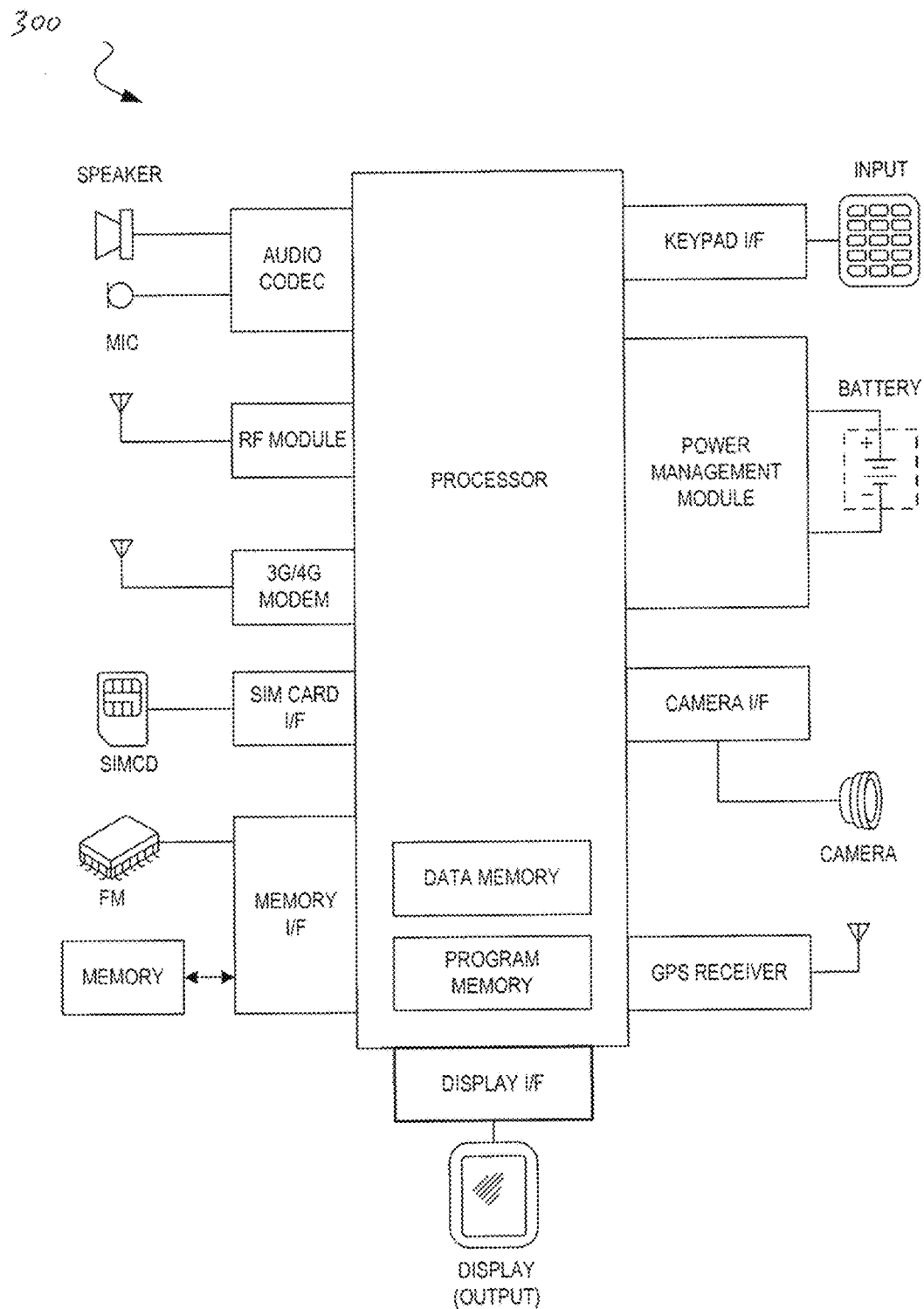
FIG. 3 is a block diagram illustrating example components of a representative mobile device in the form of a mobile (or smart) phone or tablet computer device according to various embodiments.

With reference now to FIG. 3, a block diagram illustrating example components of a representative device 300 in the form of a mobile (or smart) phone or tablet computer device that may serve as the neurofeedback system. Various interfaces and modules are shown with reference to FIG. 3; however, the mobile device or tablet computer does not require all of modules or functions for performing the functionality described herein. That is, although a mobile device 300 is described, a much simpler mobile device can be used to perform the various operations described herein. In fact, any mobile device including a housing, a processor, memory, a display, and some basic input could be used to perform the mobile device operations described herein such as, by way of example and not limitation, "dumb" phones and non-phones (e.g., Apple iTouch and Amazon Kindle devices).

Figure 4:
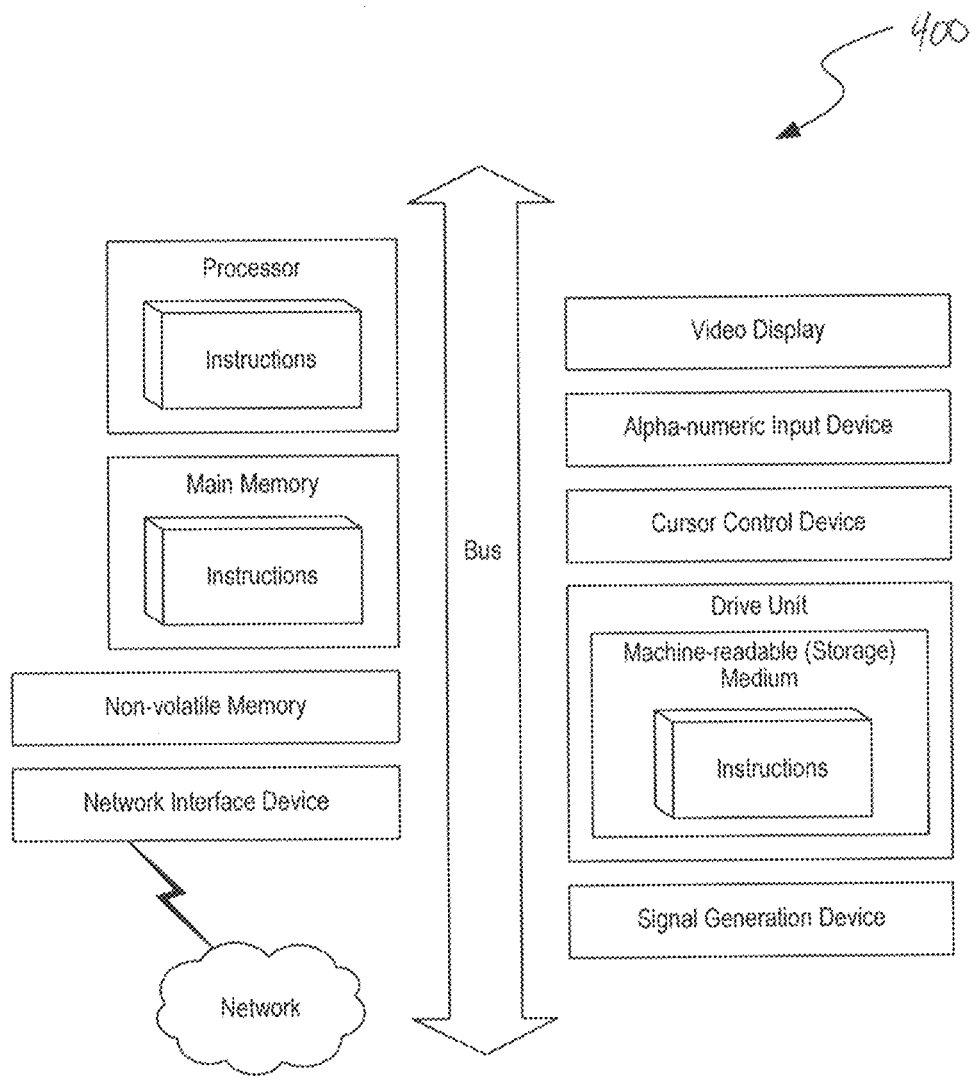
FIG. 4 is a diagrammatic representation of a machine in the example form of a computer system within which a set of instructions, for causing the machine to perform any one or more of the methodologies discussed herein, may be executed, according to various embodiments.

FIG. 4 depicts a diagrammatic representation of a machine, in the example form, of a computer system within which a set of instructions, for causing the machine to perform any one or more of the methodologies discussed herein, may be executed In the example of FIG. 4, the computer system 400 includes a processor, memory, non-volatile memory, and an interface device. Various common components (e.g., cache memory) are omitted for illustrative simplicity. The computer system 400 is intended to illustrate a hardware device on which any of the components depicted in the example of FIG. 1 (and any other components described in this specification) can be implemented. The computer system 400 can be of any applicable known or convenient type. The components of the computer system 400 can be coupled together via a bus or through some other known or convenient device.

The processor may be, for example, a conventional microprocessor such as an Intel Pentium microprocessor or Motorola power PC microprocessor. One of skill in the relevant art will recognize that the terms "machine-readable (storage) medium" or "computer-readable (storage) medium" include any type of device that is accessible by the processor.

The memory is coupled to the processor by, for example, a bus. The memory can include, by way of example but not limitation, random access memory (RAM), such as dynamic RAM (DRAM) and static RAM (SRAM). The memory can be local, remote, or distributed.

The bus also couples the processor to the non-volatile memory and drive unit. The non-volatile memory is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. Some of this data is often written, by a direct memory access process, into memory during execution of software in the computer 1300. The non-volatile storage can be local, remote, or distributed. The non-volatile memory is optional because systems can be created with all applicable data available in memory. A typical computer system will usually include at least a processor, memory, and a device (e.g., a bus) coupling the memory to the processor.

Software is typically stored in the non-volatile memory and/or the drive unit. Indeed, for large programs, it may not even be possible to store the entire program in the memory. Nevertheless, it should be understood that for software to run, if necessary, it is moved to a computer readable location appropriate for processing, and for illustrative purposes, that location is referred to as the memory in this paper. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable medium". A processor is considered to be "configured to execute a program" when at least one value associated with the program is stored in a register readable by the processor.

The bus also couples the processor to the network interface device. The interface can include one or more of a modem or network interface. It will be appreciated that a modem or network interface can be considered to be part of the computer system. The interface can include an analog modem, isdn modem, cable modem, token ring interface, satellite transmission interface (e.g. "direct PC"), or other interfaces for coupling a computer system to other computer systems. The interface can include one or more input and/or output devices. The I/O devices can include, by way of example but not limitation, a keyboard, a mouse or other pointing device, disk drives, printers, a scanner, and other input and/or output devices, including a display device. The display device can include, by way of example but not limitation, a cathode ray tube (CRT), liquid crystal display (LCD), or some other applicable known or convenient display device. For simplicity, it is assumed that controllers of any devices not depicted in the example of Figure reside in the interface.

In operation, the computer system 400 can be controlled by operating system software that includes a file management system, such as a disk operating system. One example of operating system software with associated file management system software is the family of operating systems known as Windows® from Microsoft Corporation of Redmond, Wash., and their associated file management systems. Another example of operating system software with its associated file management system software is the Linux operating system and its associated file management system. The file management system is typically stored in the non-volatile memory and/or drive unit and causes the processor to execute the various acts required by the operating system to input and output data and to store data in the memory, including storing files on the non-volatile memory and/or drive unit.

Some portions of the detailed description may be presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The algorithms and displays presented herein are not inherently related to any particular computer or other apparatus. Various general purpose systems may be used with programs in accordance with the teachings herein, or it may prove convenient to construct more specialized apparatus to perform the methods of some embodiments. The required structure for a variety of these systems will appear from the description below. In addition, the techniques are not described with reference to any particular programming language, and various embodiments may, thus, be implemented using a variety of programming languages.

In alternative embodiments, the machine operates as a standalone device or may be connected (e.g., networked) to other machines. In a networked deployment, the machine may operate in the capacity of a server or a client machine in a client-server network environment or as a peer machine in a peer-to-peer (or distributed) network environment.

The machine may be a server computer, a client computer, a personal computer (PC), a tablet PC, a laptop computer, a set-top box (STB), a personal digital assistant (PDA), a cellular telephone, an iPhone, a Blackberry, a processor, a telephone, a web appliance, a network router, switch or bridge, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways.

Also, while processes or blocks are, at times, shown as being performed in a series, these processes or blocks may instead be performed in parallel, or may be performed at different times. Further, any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for".) Accordingly, the applicant reserves the right to add additional claims after filing the application to pursue such additional claim forms for other aspects of the disclosure.

The invention claimed is:

1. A method of neurofeedback comprising:
   launching an application configured to stimulate a brain of a user;
   loading, to the application configured to stimulate the brain of the user, a trigger event;
   loading, to the application configured to stimulate the brain of the user, a feedback event;
   providing the trigger event to the user, wherein the trigger event is configured to evoke a first neurological response from the user where the first neurological response causes a first amount of dopamine to be released in the brain of the user; and
   providing the feedback event to the user at least one of simultaneously or after the trigger event is provided to the user, wherein the feedback event is configured to evoke a second neurological response to cause a second amount of dopamine to be released in the brain of the user wherein the first amount of dopamine and the second amount of dopamine are different, and such that the first neurological response evoked by the trigger event is countered by the second neurological response evoked by the feedback event.

2. The method of claim 1 wherein the trigger event is visual.

3. The method of claim 1 wherein the trigger event is auditory.

4. The method of claim 1 wherein the trigger event is a smell.

5. The method of claim 1 wherein the feedback event is visual.

6. The method of claim 1 wherein the feedback event is auditory.

7. The method of claim 1 wherein the feedback event is sensory.

8. The method of claim 1 wherein the trigger event and the feedback event are different and are selected from a group of events comprising: visual, auditory, audio/visual, smell, tactile, or a combination thereof.

9. The method of claim 1 wherein the trigger event evokes a positive neurological response and the feedback event evokes a negative neurological response, such that the first amount of dopamine is greater than the second amount of dopamine.

10. The method of claim 1 wherein the trigger event evokes a negative neurological response and the feedback event evokes a positive neurological response, such that the first amount of dopamine is less than the second amount of dopamine.

11. The method of claim 1 wherein the application is a game, the trigger event is at least one of an audio or visual component of the game, and the feedback event is a result of the game.

12. The method of claim 1 wherein the feedback event is an electric shock.

13. The method of claim 1 wherein the feedback event is a smell.

14. The method of claim 1 further comprising monitoring the neurological response of the user to the trigger event and the feedback event.

15. A neurofeedback system comprising:
   a neurofeedback processor configured to process an application to stimulate a brain of a user;
   a storage device operably coupled to the neurofeedback processor, the storage device storing at least one trigger event, wherein the at least one trigger event is configured to evoke a first neurological response in the user to cause a first amount of dopamine to be released by the user, and at least one feedback event, wherein the at least one feedback event is configured to evoke a second neurological response in the user to cause a second amount of dopamine to be released by the user such that the first amount of dopamine and the second amount of dopamine are different wherein the second neurological response counters the first neurological response; and
   a user interface wherein the user interface is configured to deliver, in response to the application, the at least one trigger and the at least one feedback to the user through the user interface.

16. The neurofeedback system of claim 15 wherein the user interface comprises a display.

17. The neurofeedback system of claim 15 wherein the user interface comprises a speaker.

18. The neurofeedback system of claim 15 wherein the user interface comprises an electric shock generator.

19. The neurofeedback system of claim 15 further comprising an EEG and electrodes coupled to the neurofeedback processor.

* * * * *